US008808733B2

(12) United States Patent
Fologea et al.

(10) Patent No.: US 8,808,733 B2
(45) Date of Patent: Aug. 19, 2014

(54) METHOD OF CONTROLLED DRUG RELEASE FROM A LIPOSOME CARRIER

(75) Inventors: Daniel Fologea, Boise, ID (US); Greg Salamo, Fayetteville, AR (US); Ralph Henry, Fayetteville, AR (US); Michael J. Borrelli, Little Rock, AR (US); Peter M. Corry, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 410 days.

(21) Appl. No.: 13/259,650

(22) PCT Filed: Mar. 31, 2010

(86) PCT No.: PCT/US2010/029413
§ 371 (c)(1),
(2), (4) Date: Sep. 23, 2011

(87) PCT Pub. No.: WO2010/114901
PCT Pub. Date: Oct. 7, 2010

(65) Prior Publication Data
US 2012/0041357 A1 Feb. 16, 2012

Related U.S. Application Data

(60) Provisional application No. 61/165,323, filed on Mar. 31, 2009.

(51) Int. Cl.
*A61K 9/127* (2006.01)

(52) U.S. Cl.
USPC .......................................................... 424/450

(58) Field of Classification Search
CPC ...................................................... A61K 9/127
USPC ............................................................ 424/450
See application file for complete search history.

(56) References Cited

U.S. PATENT DOCUMENTS

| 4,921,757 | A | * | 5/1990 | Wheatley et al. .......... 428/402.2 |
| 4,981,985 | A | | 1/1991 | Kaplan et al. |
| 5,366,881 | A | | 11/1994 | Singh et al. |
| 5,753,261 | A | | 5/1998 | Fernandez et al. |
| 5,820,879 | A | | 10/1998 | Fernandez et al. |
| 5,827,531 | A | | 10/1998 | Morrison et al. |
| 5,876,747 | A | | 3/1999 | Stracher et al. |
| 5,891,689 | A | | 4/1999 | Takle et al. |
| 6,099,864 | A | | 8/2000 | Morrison et al. |
| 6,159,443 | A | | 12/2000 | Hallahan |
| 6,277,610 | B1 | | 8/2001 | Grae |
| 6,562,316 | B1 | | 5/2003 | Edwards et al. |

(Continued)

OTHER PUBLICATIONS

Trosko, J.E., Mutation Research 480-481, pp. 219-229, 2001.*

(Continued)

*Primary Examiner* — Gollamudi Kishore
(74) *Attorney, Agent, or Firm* — Andrus Intellectual Property Law, LLP

(57) ABSTRACT

Disclosed are methods and compositions for the controlled release of a drug or agent from a liposome using light or radiation. Also disclosed are compositions comprising liposomes having a lipid layer, wherein the liposomes contain an agent, an enzyme capable of releasing the agent from the liposome, and an enzyme activator sequestered by a molecular cage. In another aspect, methods of delivering an agent to a target in a subject are disclosed.

19 Claims, 3 Drawing Sheets

(56) References Cited

U.S. PATENT DOCUMENTS

| | | |
|---|---|---|
| 6,576,257 B1 | 6/2003 | Yarmut |
| 6,579,706 B2 | 6/2003 | Grae |
| 6,602,274 B1 | 8/2003 | Chen |
| 6,835,394 B1 | 12/2004 | Discher et al. |
| 6,989,153 B2 | 1/2006 | O'Brien et al. |
| 7,018,395 B2 | 3/2006 | Chen |
| 7,049,140 B1 | 5/2006 | Hallahan |
| 7,132,289 B2 | 11/2006 | Kobayashi et al. |
| 7,223,600 B2 | 5/2007 | Berg et al. |
| 7,273,620 B1 * | 9/2007 | Zhigaltsev et al. ........... 424/450 |
| 2002/0064554 A1 | 5/2002 | O'Brien et al. |
| 2002/0115219 A1 | 8/2002 | Kobayashi et al. |
| 2002/0168734 A1 | 11/2002 | Grae |
| 2003/0219785 A1 | 11/2003 | Hallahan et al. |
| 2004/0023351 A1 | 2/2004 | Grae |
| 2004/0096425 A1 | 5/2004 | Hogset et al. |
| 2004/0110835 A1 * | 6/2004 | Keller ........................... 514/547 |
| 2004/0215292 A1 | 10/2004 | Chen |
| 2005/0075268 A1 | 4/2005 | Berg et al. |
| 2005/0186264 A1 | 8/2005 | Kiani et al. |
| 2005/0196401 A1 | 9/2005 | Chen |
| 2005/0214356 A1 | 9/2005 | Joyce |
| 2005/0272677 A1 | 12/2005 | Friesen et al. |
| 2006/0024359 A1 * | 2/2006 | Walker et al. ................. 424/450 |
| 2006/0099141 A1 | 5/2006 | O'Brien et al. |
| 2006/0188442 A1 | 8/2006 | Hallahan |
| 2006/0210549 A1 | 9/2006 | Srivastava et al. |
| 2006/0292211 A1 | 12/2006 | Hood et al. |
| 2007/0274953 A1 | 11/2007 | Berg et al. |
| 2007/0292495 A1 | 12/2007 | Ludwig et al. |
| 2008/0311182 A1 | 12/2008 | Ferrari et al. |
| 2011/0052671 A1 * | 3/2011 | Zasadzinski et al. ......... 424/450 |
| 2011/0105995 A1 * | 5/2011 | Zhu et al. ........................ 604/20 |

OTHER PUBLICATIONS

Bennett, D.E., et al., "Photoactivated enhancement of liposome fusion," Biochemistry (1995) 34(9):3102-3113.

Bisby, R.N. et al., "Fast laser-induced solute release from liposomes sensitized with photochromic lipid: effects of temperature, lipid host, and sensitizer concentration," Biochem Biophys Res Commun (1999) 262(2):406-410.

Bisby, R.N. et al., "Photosensitive liposomes as 'cages' for laser-triggered solute delivery: the effect of bilayer cholesterol on kinetics of solute release," FEBS Lett. (1999) 463(1-2):165-168.

Bisby, R.N. et al., "Active uptake of drugs into photosensitive liposomes and rapid release on UV photolysis," Photochem Photobiol. (2000) 72(1):57-61.

Bisby, R.H. et al., "Wavelength-programmed solute release from photosensitive liposomes," Biochem Biophys Res Commun (2000) 276(1):169-173.

Bondurant, B. et al., "Photoinitiated destabilization of sterically stabilized liposomes," Biochim Biophys Acta (2001) 1511(1):113-122.

Braem, et al., "Observation of the UV scintillation light from high energy electron showers in liquid Xenon," European Organization for Nuclear Research (1992) CERN-PPE/92-36 (Abstract) http://cdsweb.cern.ch/record/234171/files/cer-000148810.pdf.

Brown, E. B., et al., "Photolysis of caged calcium in femtoliter volumes using two-photon excitation," Biophysical Journal (1999) 76:489-499.

Chen, W. et al., "Using nanoparticles to enable simultaneous radiation and photodynamic therapies for caner treatment," Journal of Nanoscience and Nanotechnology (2006) 6:1159-1166.

Chen, W., et al., "Structure and luminescence of BaFBr:Eu2+ and BaFBr:Eu2+,Tb3+ phosphors and thin films," Journal of Applied Physics (2005) 97:083506-1-083506-8.

Chen, W., et al., "Utilizing nanofabrication to construct strong, luminescent materials," Nanotechnology (2006) 17:2595-2601.

Davidsen, J., et al., "Secreted phospholipase A2 as a new enzymatic trigger mechanism for localised liposomal drug release and absorption in diseased tissue," Biochimica et Biophysica Acta (2003) 1609:95-101.

Ellis-Davies, G. C. R., et al., "Tuning caged calcium:Photolabile analogues of EGTA with improved optical and chelation properties," Cell Calcium (2006) 39:75-83.

Jensen, S. S., et al., "Secretory phospholipase A2 as a tumor-specific trigger for targeted delivery of a novel class of liposomal prodrug anticancer either lipids," Molecular Cancer Therapeutics (2004) 3(11):1451-1458.

Lamparski, H. et al., "Photoinduced destabilization of liposomes," Biochemistry (1992) 31(3):685-694.

Liu, Y., et al., "Investigation of water-soluble x-ray luminescence nanoparticles for photodynamic activation," Applied Physics Letters (2008) 92:043901-1-043901-3.

Liu, Y., et al., "X-ray luminescence of LaF3:Tb3+ and LaF3:Ce3+,Tb3+ water-soluble nanoparticles," Journal of Applied Physics (2008) 103:063105-1-063105-7.

Miller, C.R. et al., "Effect of liposomal composition on photoactivated liposome fusion," Biochemistry (1996) 35 (36):11782-11790.

Miller, C.R. et al., "Visible light-induced destabilization of endocytosed liposomes," FEBS Lett. (2000) 467(1):52-56.

Morgan, C.G., et al., "Fast solute release from photosensitive liposomes: an alternative to 'caged' reagents for use in biological systems," FEBS Lett. (1995) 375(1-2):113-116.

Spratt, T. et al., "Rapid release of liposomal contents upon photoinitiated destabilization with UV exposure," Biochim Biophys Acta (2003) 1611(1-2):35-43.

Wang, F. et al., "Facile synthesis of water-soluble LaF3:Ln3+ nanocrystals," J. Material Chemistry (2006) 16:1031-1034.

International Search Report and Written Opinion for International Patent Application No. PCT/US20101029413 dated Jun. 1, 2010 (11 pages).

Extended European Search Report for European Patent Application No. 10759344.4 dated Dec. 3, 2013 (7 pages).

* cited by examiner

METHOD OF CONTROLLED DRUG RELEASE FROM A LIPOSOME CARRIER

CROSS-REFERENCE TO RELATED APPLICATIONS

This application is a national stage filing under 35 U.S.C. 371 of International Application No. PCT/US2010/029413, filed Mar. 31, 2010, which claims the benefit of U.S. Provisional Patent Application No. 61/165,323 filed Mar. 31, 2009, both of which are incorporated herein by reference in their entirety.

BACKGROUND

Current approaches for cancer treatment or treatment of other disorders may include combinations of local therapies, such as surgery and radiation therapy, with systemic therapies, such as chemotherapy and administration of pharmaceuticals or other agents. The therapeutic success of any treatment is proportional to the delivered dose of the pharmaceutical, which is limited by the toxicity to normal tissue. Controlled drug release is one method of allowing the use of increased doses of the pharmaceutical or other agent while limiting toxicity to the individual. Despite advancements that provide increased delivery of chemotherapeutic and other pharmaceuticals to target areas in the body in a controlled manner, sufficient release at the target site remains a problem.

BRIEF SUMMARY OF THE INVENTION

In one embodiment, a composition comprising a liposome having a lipid layer and containing an agent, an enzyme capable of releasing the agent from the liposome, and a molecular cage sequestering an activator capable of activating the enzyme is provided. The molecular cage may be photolabile such that the activator is released from the molecular cage after exposure to light. The liposome may also contain a nano-scintillator responsive to ionizing radiation and capable of emitting light.

In another embodiment, a method of delivering an agent to a target in a subject is provided. The method includes administering a liposome to the subject. The liposome has a lipid layer and includes an agent, an enzyme capable of releasing the agent from the liposome, and a molecular cage sequestering an activator of the enzyme. The molecular cage is photolabile. After administration of the liposome, the target is exposed to light in the UV-visible range to release the agent from the liposome by activation of the enzyme. In an alternative embodiment, the liposome also contains a nano-scintillator responsive to radiation. In this embodiment, the target is exposed to radiation, such as X-rays, to cause the release of the agent from the liposome. The release is effected by release of the activator from the molecular cage. The activator activates the enzyme and the enzyme hydrolyzes at least a portion of the liposome, releasing the agent from the liposome.

In still another embodiment, a method of treating a condition is provided. The method includes administering to a subject having the condition a liposome having a lipid layer and including an agent, an enzyme capable of releasing the agent from the liposome, and an enzyme activator sequestered by a molecular cage. The agent is capable of treating the condition. The agent is released from the liposome after exposure of a target to light or radiation. The light or radiation either directly or indirectly mediate release of the agent from the liposome to the target and allow treatment of the condition.

In yet another embodiment, a method of controlled drug release is provided in which an agent is released in a localized area. The method includes administering to a subject a liposome having a lipid layer and including an agent or drug, an enzyme capable of releasing the agent or drug from the liposome, and an enzyme activator sequestered by a molecular cage. The molecular cage is photolabile such that exposure of a target area on or in the subject to light results in the release of the drug or agent from the molecular cage in the target area. In an alternative embodiment, the liposome may also include a nano-scintillator. When the target area is exposed to radiation, the nano-scintillator produces light capable of releasing the activator from the molecular cage in the target area and the agent is released in the target area.

DETAILED DESCRIPTION

Figure 1:
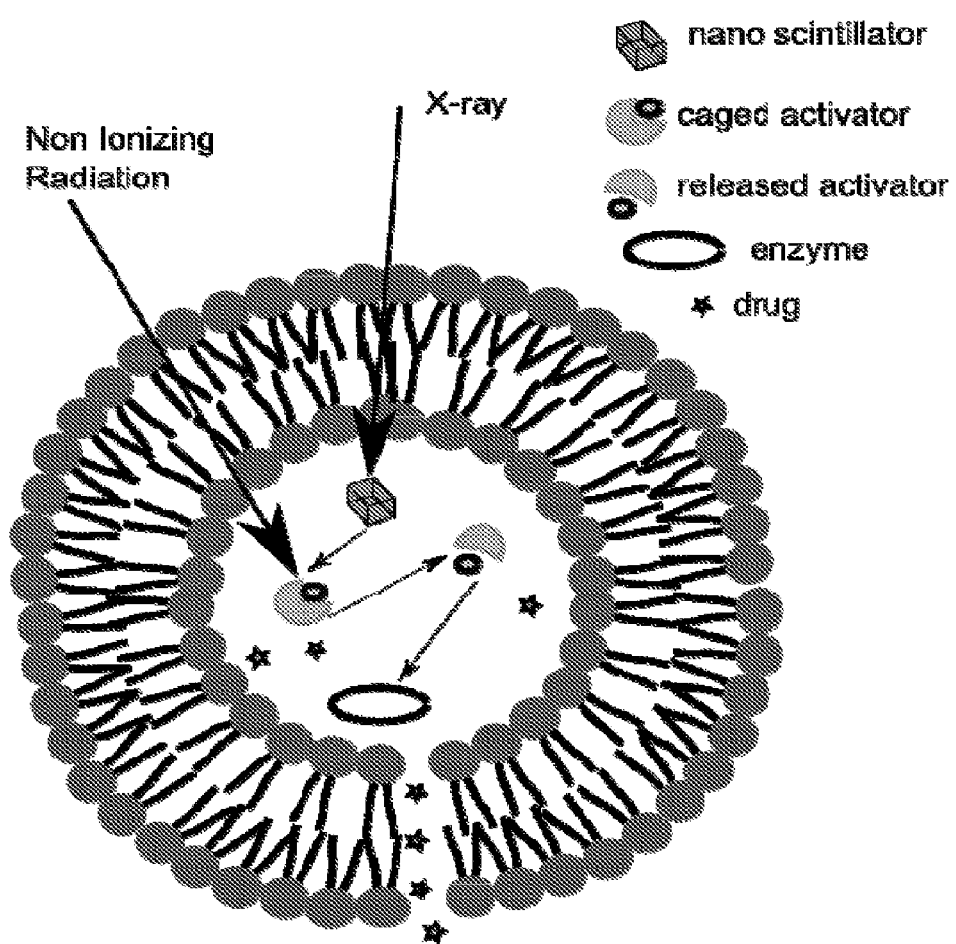
FIG. 1 is a schematic diagram of a method for controlled drug release. A liposome including a molecular cage, an activator, an agent or drug, and an enzyme is depicted. A nano-scintillator is also shown.

Compositions and methods for controlled drug release are described herein. The compositions, as depicted in FIG. 1, include a liposome having a lipid layer. The liposomes may optionally contain polypeptides within the lipid layer. The liposome contains an agent, an enzyme capable of causing the release of the agent from the liposome, and a molecular cage sequestering an activator. Because the activator is capable of activating the enzyme, release of the activator from the molecular cage causes the release of the agent from the liposome. The enzyme may be a lipase capable of degrading the liposome, such as a phospholipase. Alternatively, the enzyme may be a protease capable of degrading polypeptide containing liposomes.

The molecular cage may be photolabile such that the activator is released in response to exposure to light. For example light in the ultraviolet (UV) to infrared wavelength range may mediate release of the activator from the molecular cage. Alternatively, molecular cages responsive to pH, radiation, ionic strength, chemicals or polypeptides may be used. Molecular cages include molecules capable of sequestering a guest molecule or activator. The interaction between the molecular cage and the activator must be reversible, such that when the molecular cage/activator pair is exposed to conditions that alter the interaction between the molecular cage and the activator, the activator is release from the molecular cage. Any molecular cage may be used, such as those available from Calbiochem. The molecular cages may be capable of binding, encapsulating and/or sequestering a variety of activators, which may be released upon exposure to light having a range of wavelengths. For example, the molecular cage may release the activator after exposure to light having wavelengths from at least 200 nm, 300 nm, 325 nm, or 340 nm to no greater than 900 nm, 800 nm, 750 nm, 600 nm, 500 nm or 400 nm. For example, a molecular cage responsive to infrared or near infrared radiation, for which the biological tissue could be a transparent environment, may also be used. In the Examples, DM-Nitrophen™ from Calbiochem was used as a molecular cage for the $Ca^{2+}$. Those of skill in the art will appreciate that the molecular cages for other activators including, but not limited to, ATP, cAMP, GTP, and inositol triphosphate are available. Photolabile molecular cages are generally responsive to only a certain wavelength of light such that the release of the activator from the cage is dependent on exposure of the cage to light within a particular set of wavelengths. Thus the liposome may be administered to a subject and the agent may be sequestered within the liposome until the subject or a target area on or in the subject is exposed to light, thereby effecting release of the activator from the molecular cage, activation of the enzyme and release of the agent from the liposome in a subject or in a target area of the subject.

In some embodiments, the liposome also contains a nano-scintillator that emits light after excitation with radiation, such as ionizing radiation, e.g., X-rays. The light emitted from the nano-scintillator is suitably within the range necessary to release the activator from the molecular cage. In one embodiment shown in FIG. 1, a liposome containing a nano-scintillator, a photolabile molecular cage and an enzyme, such as a lipase, is exposed to radiation. The radiation causes the nano-scintillator to emit light which releases the activator from the molecular cage. The activator activates the enzyme which hydrolyzes the liposome and releases the agent. In one embodiment, the liposome may be exposed to X-ray radiation, which may be converted by a nano-scintillator to non-ionizing radiation, such as UV or infrared light. The light generated by the nano-scintillator releases the activator from the molecular cage. The composition may be used for controlled release of the agent to a target, such as a target tissue, in a localized area. For example, the compositions may be used to deliver an agent to a tumor, damaged tissue, site of infection or site of inflammation.

The liposomes may be made of any suitable lipid, including but not limited to, polar lipids, such as phospholipids, such as phosphoglycerides, such as phosphatidylethanolamine, phophatidylcholine, phosphatidylserine, cardiolipin or combinations thereof. Other lipid moieties may also be included in the liposomes such as triacylglycerols, waxes, sphingolipids, and sterols and their fatty acid esters, or combinations thereof. The liposome's lipid layer may also include polypeptides, such as transmembrane polypeptides, protein channels or other polypeptides capable of associating with or localizing to the lipid layer. The liposomes may additionally include a functional group such as a targeting molecule or polyethylene glycol. The targeting molecule or polyethylene glycol may be exposed on or attached to the outer surface of the liposome to target the liposome to a specific tissue or to increase the half-life of the liposome after administration to a subject. The targeting molecule may be a polypeptide or protein. Suitable targeting molecules include, but are not limited to, an antibody, a receptor such as the folate receptor or a ligand for a receptor that helps target the liposome to a specific tissue. The targeting molecule may be attached to the outer surface of the liposome, be a peripheral or integral membrane protein or may be attached by other means known to those skilled in the art such as myristoylation, acetylation, prenylation, palmitoylation, glycosylphosphatidyinositol (GPI) anchors or via cholesterol.

The liposome may be made by any method, including those known to those skilled in the art, such as sonication, extrusion and the Mozifari method. In the Examples, the liposomes were made by extrusion. Suitably, the liposomes are at least about 20 nm, 100 nm, 200 nm, 250 nm in diameter. Suitably the liposomes are no larger than about 400 nm, 500 nm, 1 micron, 2 microns or 4 microns in diameter. The size of the liposome may depend on its selected use. Suitably, the liposomes are of a size such that they are capable of selectively extravasating from leaky blood vessels near a tumor site or a site of inflammation.

The agent contained within the liposomes may be any suitable pharmaceutical or other active agent, including but not limited to, chemotherapeutic agents, toxins, radiotherapeutic agents, radiosensitizing agents, imaging agents, antimicrobials, anti-inflammatory agents, polypeptides such as recombinant proteins, cytokines or antibodies, small chemicals or any combination thereof. In the Examples, doxorubicin was used as an agent. In alternative embodiments, the active agent may be an angiogenesis inhibitor or an apoptosis inducer.

The liposomes, as prepared, contain the enzyme in an inactive state. The enzyme is suitably a lipase or a protease, which when activated, is capable of hydrolyzing at least one lipid in the lipid layer of the liposome or a peptide bond of a polypeptide within the liposome, respectively. The release of the enzyme results in at least partial degradation of the liposome such that the agent is released. Suitably, the enzyme is a phospholipase, such as phospholipase A2 or phospholipase C. Those of skill in the art will appreciate that the enzyme must be able to hydrolyze the lipids or polypeptides in the lipid layer of the liposome. In an alternative embodiment the enzyme may be a toxin, complement or other pore-forming protein or set of proteins capable of disrupting the liposome and allowing the agent to be released from the liposome through a hole or pore formed in the liposome.

Suitably conversion of the enzyme from its inactive state to an active state depends on the presence of the activator. The activator may be a co-factor that is required for enzyme activity, such as an ion or ATP. Suitable activators include, but are not limited to, Ca, Mg, Mn, Fe, Cu, Zn, ATP, cAMP, and NADPH. In the Examples, phospholipase A2 is used as the enzyme and $Ca^{2+}$ is the activator. In an alternative embodiment, the activator may be necessary for proper folding of the enzyme, to allow a pore in the liposome to open or the enzyme to otherwise compromise the integrity of the liposome. Those of skill in the art will appreciate that a variety of enzyme-activator pairs may be used.

In an alternative embodiment, the liposome may also contain a nano-scintillator. The nano-scintillator is capable of emitting light within the range needed to activate the molecular cage (i.e. in the UV to infrared range as described above) and release the activator. The nano-scintillator may be excited by ionizing or non-ionizing radiation. Suitably, the nano-scintillator is responsive to X-radiation. In the Examples, the nano-scintillator was $LaF_3Ce^{3+}$ water soluble nanoparticles made as described in Liu, Y. et al. *Journal of Applied Physics* 2008, 103, 063105 and Wang, C. et al. *Journal of Applied Physics* 2005, 97, 083506, both of which are incorporated herein by reference in their entireties. Those skilled in the art will appreciate that other nano-scintillators may be used in the compositions and methods described herein. For example, $LaF_3Tb^{3+}$ nano-scintillators have been described. The nano-scintillator chosen will determine the type of excitation source chosen for the compositions and methods of controlled drug delivery described herein. Choice of nano-scintillator will also depend on the choice of molecular cage and activator, such that the nano-scintillator releases light within the wavelengths necessary to release the activator from the molecular cage.

Methods of delivering an agent to a target in a subject are also provided. The methods include administering the liposomes described herein to a subject and exposing the target to light or radiation, depending on the liposome composition used. The light or radiation causes the activator to be released from the molecular cage either directly or indirectly. The activator then activates the enzyme and the enzyme releases the agent from the liposome at the target site to result in controlled delivery of the agent to the target. The target may be a specific tissue or organ such as the liver, kidneys, spleen or may be the site of a tumor, infection, inflammation or other site of disease.

The liposome is generally administered to the subject prior to administration of the light or radiation, which triggers release of the active agent. The liposome may be administered by any means available, including those known to those skilled in the art, such as intravenous, intratumoral, intraperitoneal, intramuscular, intra-arterial, intraventricular, dermal, or transdermal delivery. The liposome may be exposed to light or radiation by exposing the subject or a part of the subject to light or radiation. Suitably, the agent is administered in an amount effective to treat the condition and achieve a therapeutic effect in the subject, e.g., an antineoplastic effect.

Administration of the liposome compositions described herein to a subject is expected to achieve beneficial effects in a dose-dependent manner. Thus, within broad limits, administration of larger quantities of the compositions is expected to treat the condition to a greater degree than does administration of a smaller amount. It will be appreciated that the specific dosage administered in any given case will be adjusted in accordance with the specific compositions being administered, the disease to be treated, the condition of the subject, and other relevant medical factors that may modify the activity of the drug or the response of the subject, as is well known by those skilled in the art. For example, the specific dose for a particular patient depends on age, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of the compositions and of a known agent, such as by means of an appropriate conventional pharmacological protocol. It is anticipated that administration of the compositions described herein will reduce symptoms at least 50% compared to pre-treatment symptoms.

The methods may be used to treat subjects having one or more of a wide variety of medical conditions, including but not limited to cancer, such as meningiomas, hepatic cell carcinoma, pancreatic tumors, infectious diseases including fungal, bacterial, or parasitic diseases, inflammatory diseases including psoriasis and arthritis and atrial-ventricular malformations. Treatment of cancer includes, but is not limited to, killing cancer cells, slowing metastases, slowing or stopping angiogenesis, slowing or stopping the growth of the cancer cells or the size or mass of a tumor, making the cancer more responsive to a secondary therapy, such as radiation treatment. Treating an infectious disease includes, but is not limited to, reducing the length or severity of the infection, reducing morbidity, reducing mortality or killing the infectious agent. Treating an inflammatory disease includes, but is not limited to, reducing the amount or size of inflammation, reducing the severity of the inflammation, and reducing the length of the inflammatory outbreak.

EXAMPLES

Example 1

UV-Controlled Doxorubicin Release from Liposomes

Phospholipase A2 ($PLA_2$) from porcine pancreas, Sigma, 10000 u/ml) was purified, and the buffer was exchanged with 10 mM HEPES, pH=7.5, containing 150 mM KCl, by using a spin column (Viva). The drug doxorubicin HCl (Sigma) was dissolved as a stock solution (20 mM) in the same buffer. The molecular cage DM-Nitrophen (1-(2-nitro-4,5-dimethoxyphenyl)-N,N,N',N'-tetrakis [(oxycarbonyl)methyl]-1,2-ethandiamine) (EMD-Calbiochem) was prepared according to the producer recommendations. The liposome formulations were based on lecithin lipids (soy bean PC, Avanti), a suitable substrate for the $PLA_2$ enzyme. The lipids were dissolved in chloroform, vacuum dried, and subsequently hydrated in a Hepes buffer containing $PLA_2$, DM-Nitrophen (25 mM), Doxorubicin (2 mM), $CaCl_2$ (5 mM) and 150 mM KCl, pH=7.5. The $PLA_2$ enzyme amount was calculated in such a way to ensure complete hydrolysis of the PC liposomes (1 mg/ml lipids) in about 10 minutes. Due to the high affinity of DM-Nitrophen for $Ca^{2+}$, a ratio of 5:1 for these components assured a very low concentration of divalent $Ca^{2+}$ at equilibrium (dark concentration). A control sample was prepared in a similar manner but without DM-Nitrophen or $Ca^{2+}$ added, containing in turn 0.1 mM EDTA to chelate the $Ca^{2+}$ traces. The liposomes were prepared by extrusion (400 nm diameter), using a mini extruder (Avanti). The removal of the unreacted components as well as the buffer exchange was performed by centrifugation and re-suspension.

The samples were placed in the plate's wells for fluorescence reading in a kinetic mode (Gemini XP-S fluorometer, thermostated at 37° C.). The fluorescence was measured with setting the excitation at 480 nm and the emission at 590 nm. A secondary light pulse (355 nm) was obtained from the fluorometer lamp source, setting a dual excitation. The drug release was estimated from fluorescence dequenching measurements. One sample was subjected to an extensive lysis by the use of a detergent (1% Triton X100), which destabilized the liposome structure and produced a complete drug release (100%).

Figure 2:
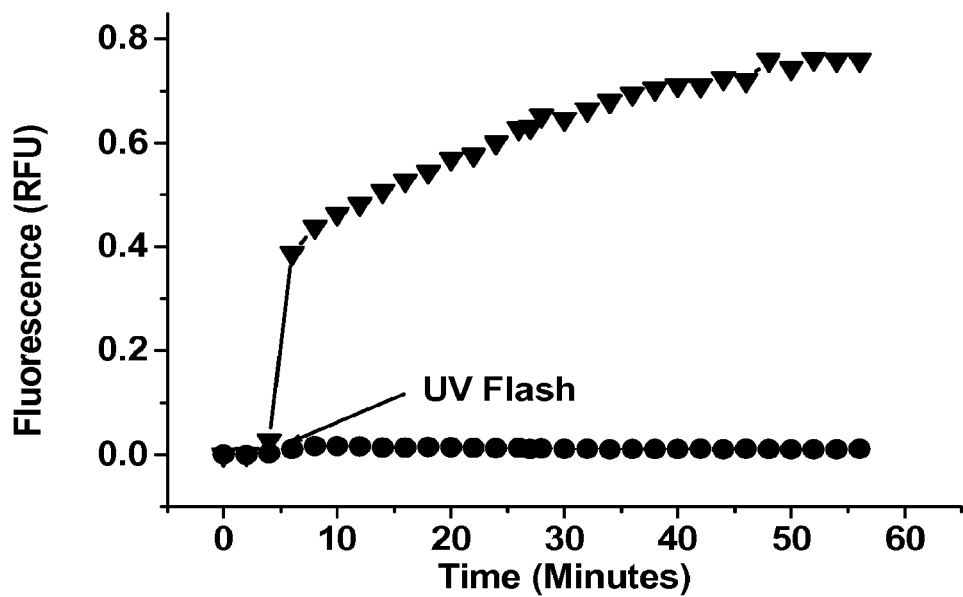
FIG. 2 is a graph of fluorescence versus time, indicating release of doxorubicin from liposomes upon exposure to UV radiation (355 nm).

Having all components (drug, enzyme, caged $Ca^{2+}$) incorporated into lecithin liposomes, a UV flash provided by the fluorometer (355 nM) was used to free the $Ca^{2+}$ from their cages and to activate the $PLA_2$ enzyme. Since the $PLA_2$ enzyme activity correlated with drug release, the kinetics of the drug release process was estimated from fluorescence dequenching (FIG. 2). As shown FIG. 2, the $PLA_2$ enzyme was activated by the $Ca^{2+}$ ions released from the cage by UV photolysis, and the drug was released from the liposomes (triangles). The sample containing EDTA as ion chelator (circles) showed no drug release upon UV exposure, presumably because the $PLA_2$ enzyme was not activated due to sequestration of $Ca^{2+}$. Together, these results showed that UV-triggered release of a $Ca^{2+}$ cofactor may be used to control drug released by lipase-mediated liposome degradation.

Example 2

UV-Fluorescence of X-Ray Excited Particles

Figure 3:
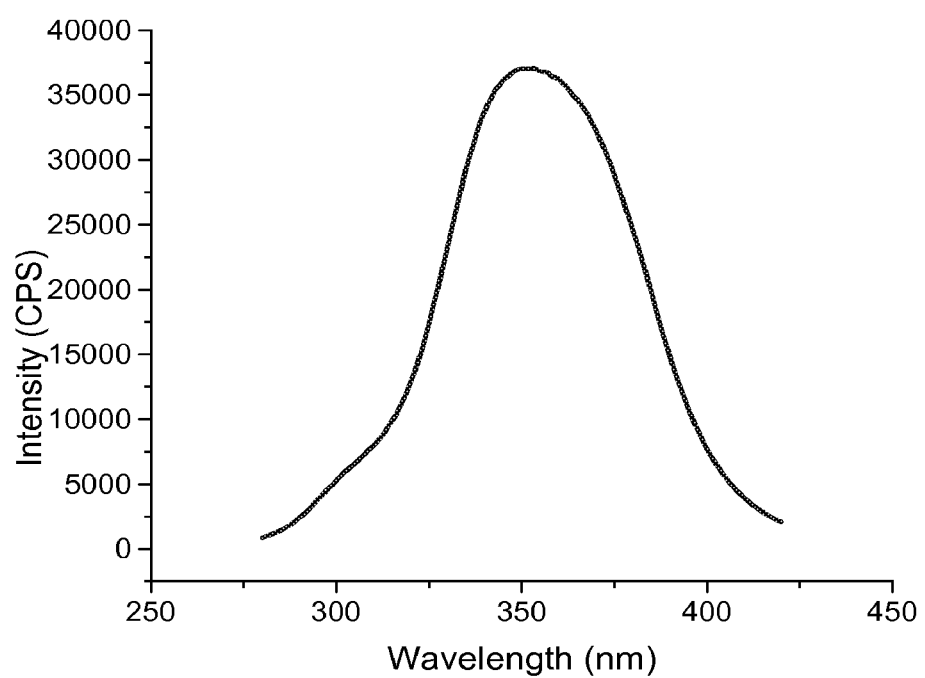
FIG. 3 is the fluorescence spectrum of X-ray excited $LaF_3Ce3+$ water soluble nanoparticles, a suitable nano-scintillator.

The nano-scintillator $LaF_3Ce^{3+}$ water soluble nanoparticles were synthesized using the procedures described in the literature (Liu, Y. et al. *Journal of Applied Physics* 2008, 103, 063105; Wang, C. et al. *Journal of Applied Physics* 2005, 97, 083506). While in solution, the nanoparticles were exposed to X-ray beams generated by a Faxitron, X-ray generating machine, with energies up to 100 KeV. The fluorescent signal was collected by using a collimator and an optical fiber, and recorded with an Ocean Optics Spectrometer. The spectrum (depicted in FIG. 3) had a maximum of approximately 353 nm, and a range covering 330-370 nm, which matches the wavelength required for photolysis of the molecular cages described in Example 1.

We claim:

1. A composition comprising a liposome having a lipid bi layer, the liposome containing
   a) an agent;
   b) phospholipase A2 or phospholipase C capable of releasing the agent from the liposome when in the presence of a calcium co-factor; and
   c) a DM-Nitrophen sequestering the calcium co-factor capable of activating the phospholipase, wherein the calcium co-factor is required for activating the lipase.

2. The composition of claim 1, wherein the molecular cage is photolabile.

3. The composition of claim 1 wherein the phospholipase A2 or phospholipase C is capable of hydrolyzing at least one lipid in the liposome.

4. The composition of claim 1, wherein the agent comprises a chemotherapeutic agent, a polypeptide, a toxin, a radiotherapeutic agent, a radiosensitizing agent, an imaging agent or combinations thereof.

5. The composition of claim 1, wherein the liposome further comprises a targeting molecule.

6. The composition of claim 1, wherein the liposome further comprises at least one polypeptide capable of localizing to the lipid layer and a protease.

7. The composition of claim 1, further comprising a nano-scintillator capable of emitting UV light upon excitation.

8. The composition of claim 7, wherein the nano-scintillator is responsive to radiation.

9. The composition of claim 8, wherein the nano-scintillator is responsive to X-radiation.

10. A method of delivering an agent to a target in a subject, the method comprising:
    a) administering the liposome of claim 1 to the subject; and
    b) exposing the target to light, whereby the light releases the calcium co-factor from DM-Nitrophen, the co-factor activates phospholipase A2 or phospholipase C and phospholipase A2 or phospholipase C releases the agent from the liposome.

11. A method of delivering an agent to a target in a subject, the method comprising:
    a) administering the liposome of claim 7 to the subject; and
    b) exposing the target to radiation, whereby the radiation activates the nano-scintillator to emit UV light which releases the calcium co-factor DM-Nitrophen, the calcium co-factor activates phospholipase A2 or phospholipase C and phospholipase A2 or phospholipase C releases the agent from the liposome.

12. The method of claim 10, wherein the target comprises a tumor.

13. The method of claim 10, wherein the liposome is administered to a patient before exposing the target to light.

14. The method of claim 11, wherein the liposome is administered to a patient before exposing the target to radiation.

15. A method of controlled drug release, the method comprising the method of claim 10, wherein the agent is released in a localized area.

16. A method of treating a condition responsive to the agent, the method comprising administering the liposome of claim 1.

17. The method of claim 16, wherein the condition is cancer.

18. The method of claim 11, wherein the target comprises a tumor.

19. A method of controlled drug release, the method comprising the method of claim 11, wherein the agent is released in a localized area.

* * * * *